United States Patent [19]

LaFoy

[11] Patent Number: 4,562,300

[45] Date of Patent: Dec. 31, 1985

[54] MERCAPTAN EXTRACTION PROCESS

[75] Inventor: Carl J. LaFoy, Houston, Tex.

[73] Assignee: Phillips Petroleum Company, Bartlesville, Okla.

[21] Appl. No.: 725,274

[22] Filed: Apr. 19, 1985

[51] Int. Cl.$^4$ ................................................ C07C 7/10
[52] U.S. Cl. ..................................... 585/854; 208/235
[58] Field of Search ...................... 208/230, 235, 238; 585/854, 867

[56] References Cited

U.S. PATENT DOCUMENTS

| | | | |
|---|---|---|---|
| 2,152,166 | 3/1939 | Yabroff | 585/854 |
| 2,164,851 | 7/1939 | Yabroff | 585/854 |
| 2,305,549 | 12/1942 | Nixon | 208/263 |
| 2,320,267 | 5/1943 | Cohen | 208/263 |
| 2,616,833 | 11/1952 | Chenicek et al. | 196/29 |
| 2,794,767 | 6/1957 | Gleim et al. | 196/32 |
| 2,921,020 | 1/1960 | Urban et al. | 208/205 |
| 2,921,021 | 1/1960 | Urban et al. | 208/205 |
| 2,934,496 | 4/1960 | Urban | 208/235 |
| 2,937,986 | 5/1960 | Lukk | 208/235 |
| 3,107,273 | 10/1963 | Cole et al. | 208/235 |
| 4,040,947 | 8/1977 | Christman | 208/235 |
| 4,081,354 | 3/1978 | Christman | 585/854 |
| 4,104,155 | 8/1978 | Christman | 208/235 |
| 4,324,650 | 4/1982 | Carlson | 208/206 |
| 4,347,226 | 8/1982 | Audeh et al. | 208/235 |
| 4,362,614 | 12/1982 | Asdigian | 208/235 |
| 4,404,098 | 9/1983 | Asdigian | 208/235 |

OTHER PUBLICATIONS

Advertisement for Merox ® and HF Alkylation.

*Primary Examiner*—D. E. Gantz
*Assistant Examiner*—Anthony McFarlane
*Attorney, Agent, or Firm*—L. M. Lavin

[57] ABSTRACT

A caustic wash process to remove mercaptans from a mixture of hydrocarbons, an improvement comprising washing the regenerated caustic with a fraction of said hydrocarbon to remove residual disulfides to improve the overall removal of sulfur from the hydrocarbon feed stream.

8 Claims, 2 Drawing Figures

MERCAPTAN EXTRACTION PROCESS

This invention relates to the removal of mercaptans from a hydrocarbon-containing feed stream. In particular, it relates to the use of a caustic solution to remove mercaptans from a hydrocarbon-containing feedstream.

It is conventional practice at the present time to treat sour hydrocarbon streams to remove mercaptans by contacting the hydrocarbon stream with an alkaline solution in which mercaptides are soluble. The alkaline solution is then separated from the treated stream and subjected to regeneration. The alkaline solution is regenerated by oxidizing the mercaptides to disulfides using a catalyst. One method is to use a metal chelate such as disalicylal ethylene diamino cobalt. Recently, it has been found that certain phtalocyanine compounds are extremely effective catalysts for oxidizing mercaptans or mercaptides and that these compounds regenerate the alkaline solution by oxidation. Other methods exists and are known in the art. The disulfides thus formed coalesce and settle. The disulfides are then separately withdrawn from the alkaline solution and the regenerated alkaline solution is reused in the process.

This regeneration process leaves the alkaline solution still containing about 25 percent of the original amount of the sulfur compounds absorbed by the solution. The sulfur compounds remaining in the alkaline solution are soluble in the solution and normally, are recirculated to the extractor which in turn reduces the ability of the extractor to remove further sulfur from the hydrocarbon stream. This in turn can affect downstream catalysts which could be poisoned by either mercaptans or solubilizd organic disulfides that are not removed by the alkaline solution.

The object of this invention is to remove the remaining sulfur compounds from the regenerated alkaline solution. Another object of this invention is to remove sulfur from the hydrocarbon stream. Another related object of this invention is to protect sensitive catalysts from poisoning by mercaptans or disulfides present in a hydrocarbon stream. These and other objects will become apparent from the following description of the invention.

SUMMARY OF THE INVENTION

According to the instant invention, the regenerated alkaline solution containing a minor amount of disulfides in solution is contacted with a previously treated hydrocarbon stream to remove the disulfides from the caustic. In the preferred embodiment, the hydrocarbon stream that is used in treating the regenerated caustic will not be subject to isomerization or will be downstream from any treatment that utilizes sulfur sensitive catalyst. This invention is particularly useful in treating an isopentane/normal pentane hydrocarbon feed stream that contains mercaptans.

DETAILED DESCRIPTION OF THE INVENTION

Figure 1:
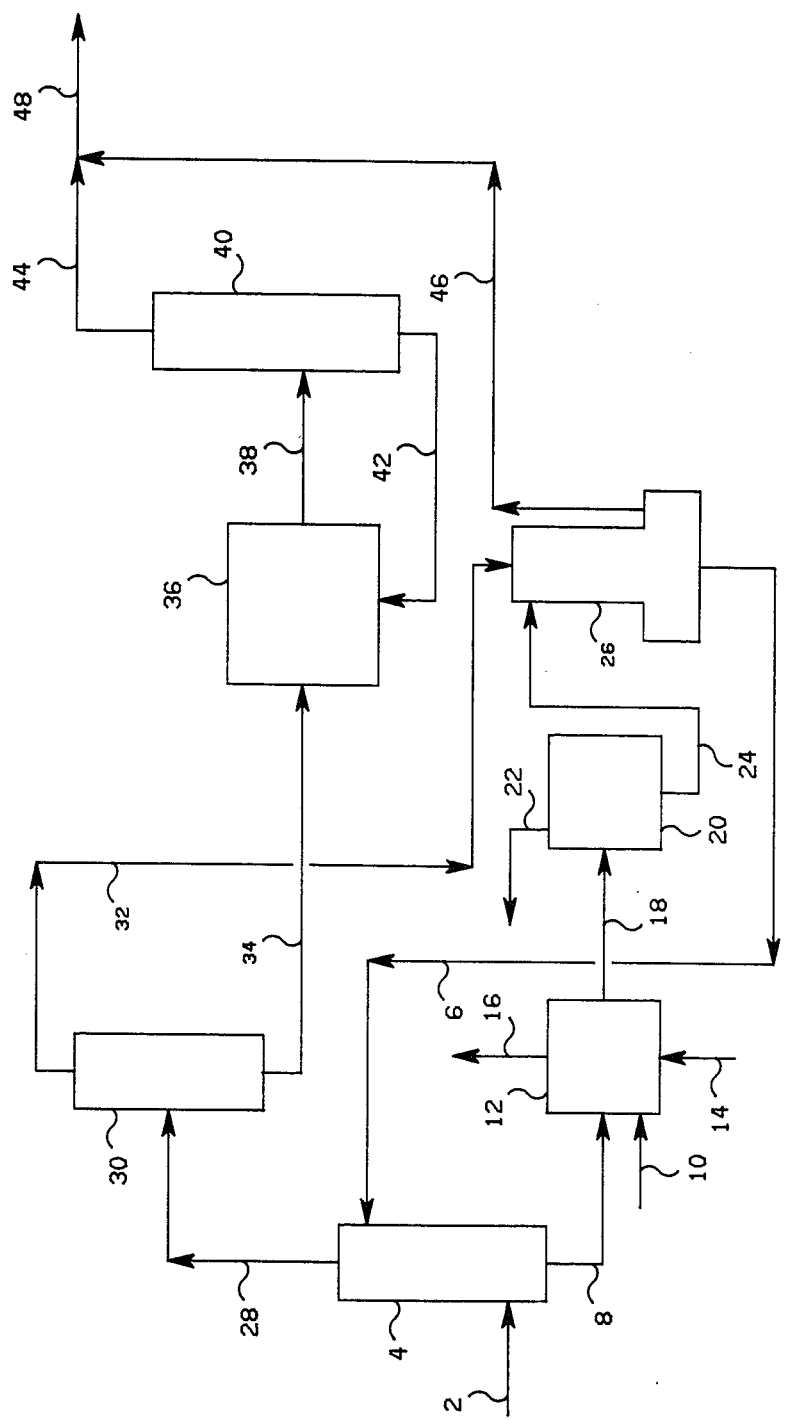
FIG. 1 shows a typical process for treating mixed pentanes that utilizes the instant invention.

Processes which extract mercaptans from hydrocarbon streams by contacting the stream with an alkaline solution are very widely used. In a large number of these processes, the alkaline solution is comprised of water and an alkaline reagent. This solution is regenerated by the catalyzed oxidation of the mercaptans to disulfides and the subsequent separation of the disulfides from the solution. U.S. Pat. Nos. 2,921,021 and 2,921,020, both hereby incorporated by reference, show a system that can be improved using the instant invention. Several other references, including U.S. Pat. Nos. 4,040,947, 4,362,614, 4,404,098 show the state of the art.

There are several advantages to the present invention. The first is that by contacting the alkaline solution with the treated hydrocarbon stream, sulfur compounds are removed from the alkaline solution to further enhance the solution's ability to remove sulfur from the hydrocarbon feedstream. A second advantage is that removing the remaining sulfur from the alkaline stream using the already treated hydrocarbon stream, maintains the efficiency of sulfur sensitive catalyst while increasing the sulfur content of the treated hydrocarbon stream by only a small amount. Another advantage is that using this hydrocarbon stream saves on the cost of installing a separate hydrocarbon treating stream.

The hydrocarbon streams that can be utilized in this invention include any feedstream, that contains predominately hydrocarbons, that also contains undesirable levels of sulfur compounds. The present invention is especially suitable for the sweetening of hydrocarbon distillates and particularly sour gasoline, including cracked gasoline, straight run gasoline or mixtures thereof, naphtha, jet fuel, kerosene, aromatic solvent, stove oil, range oil, fuel oil, etc. Other hydrocarbon distillates include lube oil as well as normally gaseous fractions. In still another embodiment, the novel features of the present invention can be utilized for purifying other organic fractions containing certain acidic impurities. These organic compounds include alcohols, ketones, aldehydes, etc.

The alkaline solution composition generally is an aqueous solution with the alkaline present in the range generally from about 5 to about 50 weight percent, but preferably between about 10-15 weight percent. The preferred caustic material is an aqueous solution of sodium hydroxide in water. Other materials such as potassium hydroxide and lithium hydroxide in aqueous solution can be used.

According to the instant invention, the alkaline solution is contacted with the hydrocarbon feedstream in a countercurrent extractor. This extraction process takes place at temperatures ranging from about 100° F. to about 150° F. and pressures ranging from about 60 psig to about 110 psig. Preferably the conditions in the extractor are 125° F. and 85 psig. The weight ratio of feed to alkaline solution fed into the extractor should range from about 2.0 to about 4.0. In the first contactor, mercaptans such as methyl and isopropyl and alkane mercaptan are removed to form RSNa and water were where R is a $C_1$ to $C_6$ hydrocarbon.

The contacting apparatus can be chosen from any common contacting apparatus but is preferably a countercurrent liquid-liquid trayed contactor. This apparatus preferably contains perforated trays. The alkaline solution can flow, for example, from the top to the bottom of the apparatus countercurrently to the hydrocarbon feed. The treated hydrocarbon feedstream leaves the extractor and can be further treated and separated through conventional means.

The alkaline solution exits from the extractor and is then injected into an oxygenation reactor. It is there the mercaptans are oxygenated to disulfides. A catalyst can also be used in the oxygenation reactor. The thus formed organic disulfides are insoluble in the aqueous alkaline solution. Some of the sulfur materials will remain unreacted from the oxygenation reactor. This stream is then sent to a settler to separate the disulfides from the alkaline stream.

The mercaptan rich alkaline solution is heated to 145°–150° F. in the oxygenation reactor. Air is injected and the flow is cocurrent in the oxygenation reactor, which can be any conventional reactor but preferably a packed column containing one inch diameter Raschig rings. The pressure in the oxygenation reactor is about 70–75 psig at 145°–150° F.

After the oxygenation step the alkaline and sulfur material go to a phase separator where alkaline solution containing about 60 ppm total of organic sulfides and disulfides are separated from an organic disulfide phase.

The inventive feature involves an extractor unit in which an already treated hydrocarbon stream is used to cleanup further the recycled alkaline solution by contacting the alkaline solution with hydrocarbon stream or part thereof, preferably isopentane, to remove traces of organic disulfide. The conditions of the contacting will generally be in the range of 100°–110° F. and 50 psig. To 70 psig. Any means can be provided for the contacting but the preferred system is a cocurrent extractor. This extractor can be packed with, for example, 1–2 inch diameter Raschig rings. The thus treated alkaline solution now free of disulfides is then recycled to the first extractor unit to treat more hydrocarbon feedstreams.

The following examples give a detailed description of one embodiment to further explain this invention. The invention is not limited to this particular embodiment, however.

EXAMPLE I

FIG. 1 is a schematic diagram for the processing of about 12000 BPD of mixed iso-and normal-pentane containing about 60 wt % n-pentane and 40 wt % isopentane and typically about 330 ppm of organic mercaptans. This mixed pentane stream enters a liquid-liquid mercaptan extraction column 4 (via conduit 2). This column has seven perforated trays spaced 5-feet apart along the column and contain over 200 holes per tray the holes having about ⅜-inch diameter each. The column operates at about 85 psig pressure and about 125° F. and is about 8-feet in diameter. An aqueous caustic solution containing typically about 12 wt % caustic enters column 4 above the top tray via conduit 6. This caustic or alkaline solution is virtually free of any organic disulfide content which is the result of the invention discussed previously. There is a small amount of organic sodium mercaptides which remain essentially in the aqueous caustic stream 6. The aqueous sodium hydroxide or caustic soda solution passes countercurrently downward through the dual flow perforated trays to the upflowing mixed pentanes. The mixed pentanes now essentially free of organic mercaptans and disulfides exit column 4 via conduit 28 while the aqueous caustic solution exits the bottom of column 4 via conduit 8. This caustic solution now rich in organic mercaptans is heated to about 150° F. by a heat exchanger (not shown).

The caustic solution rich in mercaptans enters oxidizer 12 along with small amounts of catalyst such as disalicylal ethylene diamine cobalt via conduit 10 and air via conduit 14. Here the organic mercaptans are converted to organic disulfides. Oxidizer 12 can be a column packed with Rachig rings or the like. Excess air exits the oxidizer via conduit 16. The regenerated caustic solution now essentially free of organic mercaptans enters via conduit 18 a settler 20 where a liquid phase of organic disulfides exit the settler via conduit 22. Regenerated caustic solution containing a small amount of dissolved organic disulfides exits the bottom of the settler 20 via conduit 24 and enter an organic disulfide extraction column and separator 26 to be discussed later in FIG. 2 and in the example.

The isopentane-n-pentane stream now essentially free of sulfur containing compounds enters pentane splitter fractionator 30 via conduit 28 in which there is a sand filter and water washer and dryer (not shown). This fractionator 30 distills the mixed pentanes into essentially iso-pentane which exits fractionator 30 overhead via conduit 32 and essentially n-pentane which exits fractionator 30 bottom via conduit 34.

The n-pentane is heated in a heat exchanger (not shown) and enters isomerization reactor 36 where substantial conversion of n-pentane to isopentane takes place in the presence of hydrogen (the injection of hydrogen is not shown). The isomerization reaction conditions are about 720° F. and about 535 psig and takes place over a fixed bed of platinum based catalyst of about 16-feet in depth. The isopentane-n-pentane containing reactor effluent exits reactor 36 via conduit 38 in which there is a cooler (not shown) and a stabilizer column (not shown) and enters pentane splitter fractionator 40. Overhead isopentane exits fractionator 40 via conduit 44 and essentially n-pentane is recycled via conduit 42 to isomerization reactor 36. Isopentane in conduit 44 is joined with isopentane containing small amounts (about 200 ppm) of organic disulfide via conduit 46 as shown in FIG. 2.

Figure 2:
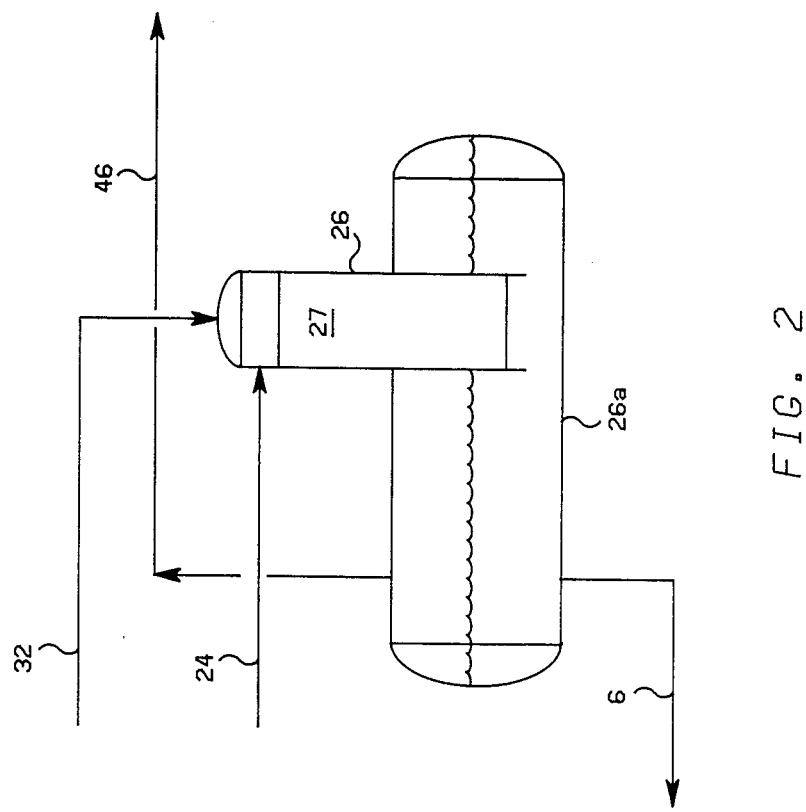
FIG. 2 shows details of a typical unit of the instant invention.

FIG. 2 illustrates a cocurrent contactor 26 and settler 26a. Contactor 26 can be packed (27) with a plurality of radial wires extending from the center of the contactor along its vertical center-line containing a wire connecting member from the top to bottom of a typical 30-inch diameter column which is 6-feet-six inches in height. Alternatively the contactor 26 can be packed with pall rings (27), Rachig rings and the like suitably supported near the bottom of contactor 26.

A stream of essentially isopentane enters contactor 26 via conduit 32 where it is admixed with regenerated aqueous caustic solution containing small amounts of organic disulfides and organic mercaptides via conduit 24. In this cocurrent contactor, isopentane extracts the organic disulfides and the caustic solution and isopentane are settled in separator 26a. The separator 26a is about 8 feet in diameter and 35-feet in length. Conditions in contactor-separator 26–26a are preferably about 115° F. and 60 psig. Caustic solution exits separator 26a via conduit 6 for recycle to mercaptan extractor 4 and the isopentane exits separator 26a via conduit 46. Isopentane from column 40 admixes via conduit 44 and isopentane containing small amounts of organic disulfides via conduit 46 pass via conduit 48 to storage (not shown).

CALCULATED EXAMPLE II

A calculated material balance to illustrate the invention of using essentially isopentane free of sulfur compounds to remove organic disulfides remaining in the regenerated aqueous caustic solution and thereby protect the sulfur sensitive isomerization catalyst in reactor 36 is given in Table I.

TABLE I

| | Calculated Material Balance IN LB/HR | | | |
|---|---|---|---|---|
| | Stream Number | | | |
| COMPONENT | 24 | 32 | 6 | 46 |
| isopentane | — | 54055 | — | 54055 |
| n-pentane | — | 545 | — | 545 |
| sodium hydroxide | 4426 | — | 4426 | — |
| water | 32457 | — | 32457 | — |
| organic disulfides (RSSR) | 1.77 | — | — | 1.77 |
| organic sodium mercaptides | 0.44 | — | 0.44 | — |
| | 36885.21 | 54600 | 36883.44 | 54601.77 |

The above figures illustrate how dissolved organic disulfides in regenerated caustic (24) are extracted into the isopentane (46) leaving regenerated caustic free of organic disulfides which now no longer pass to isopentane-n-pentane stream (28) and no longer to the n-pentane (34) and thereby protect and lengthen the activity of the catalyst in reactor (36) to perform isomerization of normal pentane to isopentane.

I claim:

1. A process for removing mercaptans from a hydrocarbon feed stream using a caustic solution comprising contacting said hydrocarbon feedstream with said caustic, separating said hydrocarbon feedstream from said caustic, oxidizing said caustic stream to convert removed mercaptans to disulfides, settling the thus treated caustic to separate the majority of said disulfides and contacting the remaining caustic solution containing sulfides and disulfides with a portion of said separated hydrocarbon feedstream to remove the remaining disulfides.

2. A process according to claim 1 where said hydrocarbon feedstream is an isopentane and normal pentane mixture.

3. A process according to claim 2 where said isopentane and normal pentane mixture is separated into an isopentane portion and a normal pentane portion and said isopentane portion is used to contact said caustic solution containing soluble sulfides and disulfides.

4. A process according to claim 3 where said remaining caustic solution containing sulfides and disulfides is contacted with said separated hydrocarbon feedstream at a temperature ranging from about 100° to about 110° F. and a pressure ranging from about 50 to about 70 psig.

5. A process according to claim 4 where said contacting is cocurrent and takes place in a packed column.

6. A process according to claim 5 where said column is packed with Raschig rings.

7. A process according to claim 1 where said caustic solution is an aqueous solution containing from about 5 to about 50 weight percent caustic.

8. A process according to claim 7 where said caustic solution is an aqueous solution containing from about 10 to about 15 weight percent caustic.

* * * * *